United States Patent [19]

Piper et al.

[11] Patent Number: 5,287,849
[45] Date of Patent: Feb. 22, 1994

[54] MEDICINAL AEROSOL DELIVERY SYSTEM AND METHOD OF USE

[75] Inventors: Samuel D. Piper, Sacramento; David A. Blackney, Orangevale; Lysa S. Kinoshita, Sacramento; Russell T. Reid, Garden Valley; Otto G. Raabe, Davis; James I. C. Lee, Sacramento, all of Calif.

[73] Assignee: Vortran Medical Technology, Inc., Sacremento, Calif.

[21] Appl. No.: 919,585

[22] Filed: Jul. 24, 1992

[51] Int. Cl.$^5$ .................................. A62M 16/10
[52] U.S. Cl. ..................... 128/203.12; 128/200.24; 128/204.18; 128/207.14; 128/912
[58] Field of Search ............ 128/203.12, 207.14, 128/204.18, 911, 912, 200.21, 200.22, 200.23, 200.14, 200.24

[56] References Cited

U.S. PATENT DOCUMENTS

| | | | |
|---|---|---|---|
| 3,388,705 | 6/1968 | Grosshandler | 128/207.14 |
| 3,714,944 | 2/1973 | Price et al. | 128/203.12 |
| 4,200,094 | 4/1980 | Gedeon | 128/201.13 |
| 4,232,667 | 11/1980 | Chalon et al. | 128/203.26 |
| 4,385,629 | 5/1983 | Wolf, Jr. | 128/207.14 |
| 4,516,573 | 5/1985 | Gedeon | 128/201.13 |
| 4,621,632 | 11/1986 | Bartels et al. | 128/203.27 |
| 4,681,100 | 7/1987 | Brychta | 128/204.25 |
| 4,829,998 | 5/1989 | Jackson | 128/203.12 |
| 4,953,547 | 9/1990 | Poole, Jr. | 128/203.12 |
| 5,044,361 | 9/1991 | Werner | 128/204.16 |

FOREIGN PATENT DOCUMENTS

| | | | |
|---|---|---|---|
| 519742 | 12/1992 | European Pat. Off. | 128/203.12 |
| 3636669 | 10/1986 | Fed. Rep. of Germany | |
| 8501824 | 1/1987 | Netherlands | 128/203.12 |
| 8604822 | 8/1966 | PCT Int'l Appl. | |
| 2169515 | 7/1986 | United Kingdom | 128/207.14 |

Primary Examiner—Edgar S. Burr
Assistant Examiner—Eric P. Raciti
Attorney, Agent, or Firm—John P. O'Banion

[57] ABSTRACT

A method and apparatus for administering medicinal aerosol to a patient's lungs through an endotracheal tube (22) connected to a ventilator (100) or other respiratory apparatus, in which a charging volume (26) connected to a nebulizer (102) for generating medicinal aerosol is inserted between the ventilator (100) and the endotracheal tube (22), such that the charging volume (26) is filled with medicinal aerosol during patient exhalation, and the medicinal aerosol in the charging volume (26) is delivered into the endotracheal tube during patient inhalation. Additional amounts of medicinal aerosol are delivered into the endotracheal tube (22) during patient inhalation through hose (24) between the charging volume (26) and the nebulizer (102).

14 Claims, 3 Drawing Sheets

MEDICINAL AEROSOL DELIVERY SYSTEM AND METHOD OF USE

BACKGROUND OF THE INVENTION

1. Field of the Invention

This invention pertains generally to delivery of medicinal aerosols, and more particularly to a system for delivering medicinal aerosols to a patient through an endotracheal tube.

2. Description of the Background Art

It is known that the thin membrane of the lungs can be easily penetrated by medicinal aerosols and provides a convenient and generally safe vehicle for obtaining rapid absorption of medication by the body. Medication or drugs are generally delivered to the lung membrane in the form of a fine mist or aerosol which is breathed into the lungs through the nose or mouth of the patient. Quite typically, a nebulizer is used to convert a liquid into a fine aerosol, and the aerosol is introduced into the lungs through an endotracheal tube.

Delivery of medicinal aerosols in this manner is most commonly made through an endotracheal tube connected to a "patient wye." Referring to FIG. 1, which schematically shows a known configuration, a patient wye 10 typically has an inhalation port 12 which is connected to an inhalation tube 14, an exhalation port 16 which is connected to an exhalation tube 18, and an endotracheal port 20 which is connected to an endotracheal tube 22. Inhalation tube 14 and exhalation tube 18 are connected to a ventilator, respirator, or the like. An aerosol supply hose 24, which is connected to a nebulizer or other device for generating a continuous flow of medicinal aerosol, is connected to input port 12.

When medicinal aerosol is delivered directly to inhalation port 12 of patient wye 10 in this manner, the ventilator will ventilate the patient by providing a constant airflow in the inhalation tube 14 and periodically inflating the patient by occluding the flow through the exhalation tube 18. In this configuration, the medicinal aerosol is diluted by the inhalation flow coming from the ventilator. In addition, approximately ninety percent of the medicinal aerosol is wasted because it continues to be administered during exhalation and, therefore, passes into the exhalation tube 18 where it is lost.

As can be seen, therefore, a need exists for an aerosol delivery system which administers medicine during the inhalation cycle and stores medicine during the exhalation cycle. The present invention satisfies that need and significantly increases the efficiency of delivery of medicinal aerosol.

SUMMARY OF THE INVENTION

The present invention generally pertains to a method and system for delivering medicinal aerosol to a patient through an endotracheal tube wherein the medicinal aerosol is not wasted during the exhalation cycle of a ventilator or other respiratory therapy device. By way of example, and not of limitation, in general terms the present invention comprises a charging system having gas ports and an aerosol port which is inserted between the patient wye (or respiratory device) and the endotracheal tube. The charging system is equipped with a port on the patient side of the circuit to provide a means to connect an aerosol supply hose. The aerosol supply hose is connected to a nebulizer or other device for generating medicinal aerosol, such that the charging system is filled with medicinal aerosol during patient exhalation, and the medicinal aerosol in the charging system is delivered into the endotracheal tube during patient inhalation. Additional amounts of medicinal aerosol are delivered into the endotracheal tube during inhalation through the aerosol supply hose since the nebulizer to which it is connected provides a continuous flow of aerosol into the charging system. During patient exhalation, the flow of aerosol from the nebulizer flushes the exhaled gas out of the charging system and fills it with medicinal aerosol. During patient inhalation, the respiratory device inflates the patient as it would normally, pushing the aerosol contained in the charging system into the patient's lungs. This cycle, which is then repeated indefinitely, results in delivery of up to ninety-seven percent of the medicinal aerosol to the patient. As can be seen, this is an increase in efficiency of greater than nine hundred percent over conventional delivery systems.

An object of the invention is to provide for efficient delivery of medicinal aerosol to a patient.

Another object of the invention is to prevent dilution of medicinal aerosols delivered to a patient.

Another object of the invention is to prevent medicinal aerosol from being discharged through a respiratory exhalation tube.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
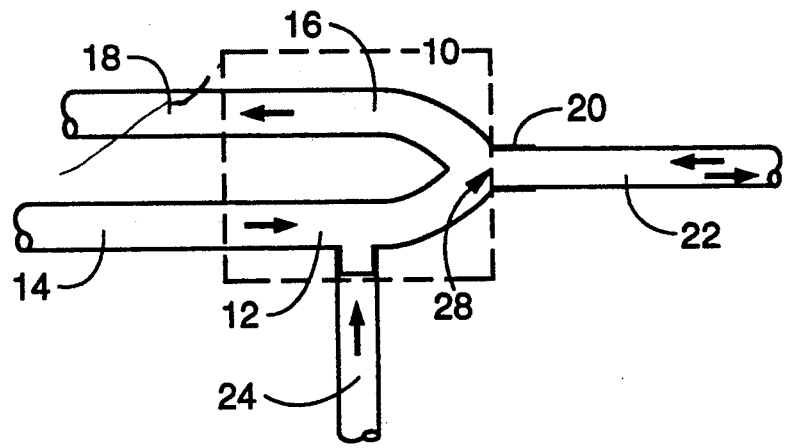
FIG. 1 is a schematic representation of a prior art aerosol delivery system.
Figure 2:
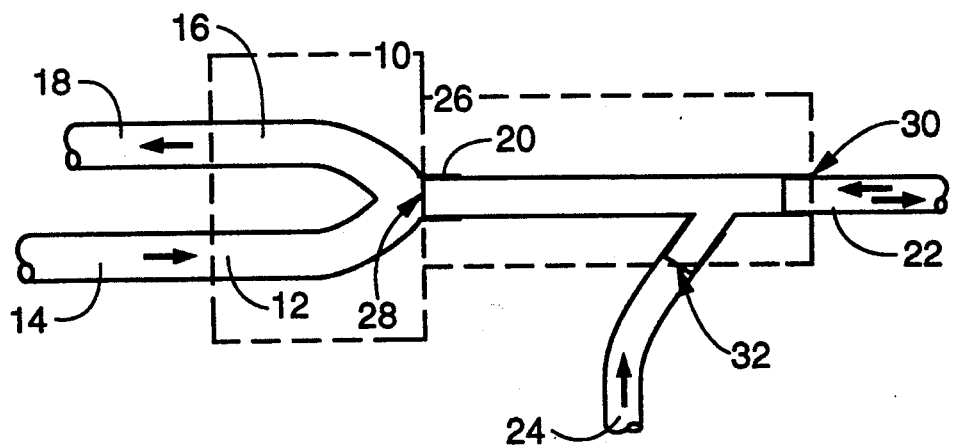
FIG. 2 is a schematic representation of the aerosol delivery system of the present invention.
Figure 3:
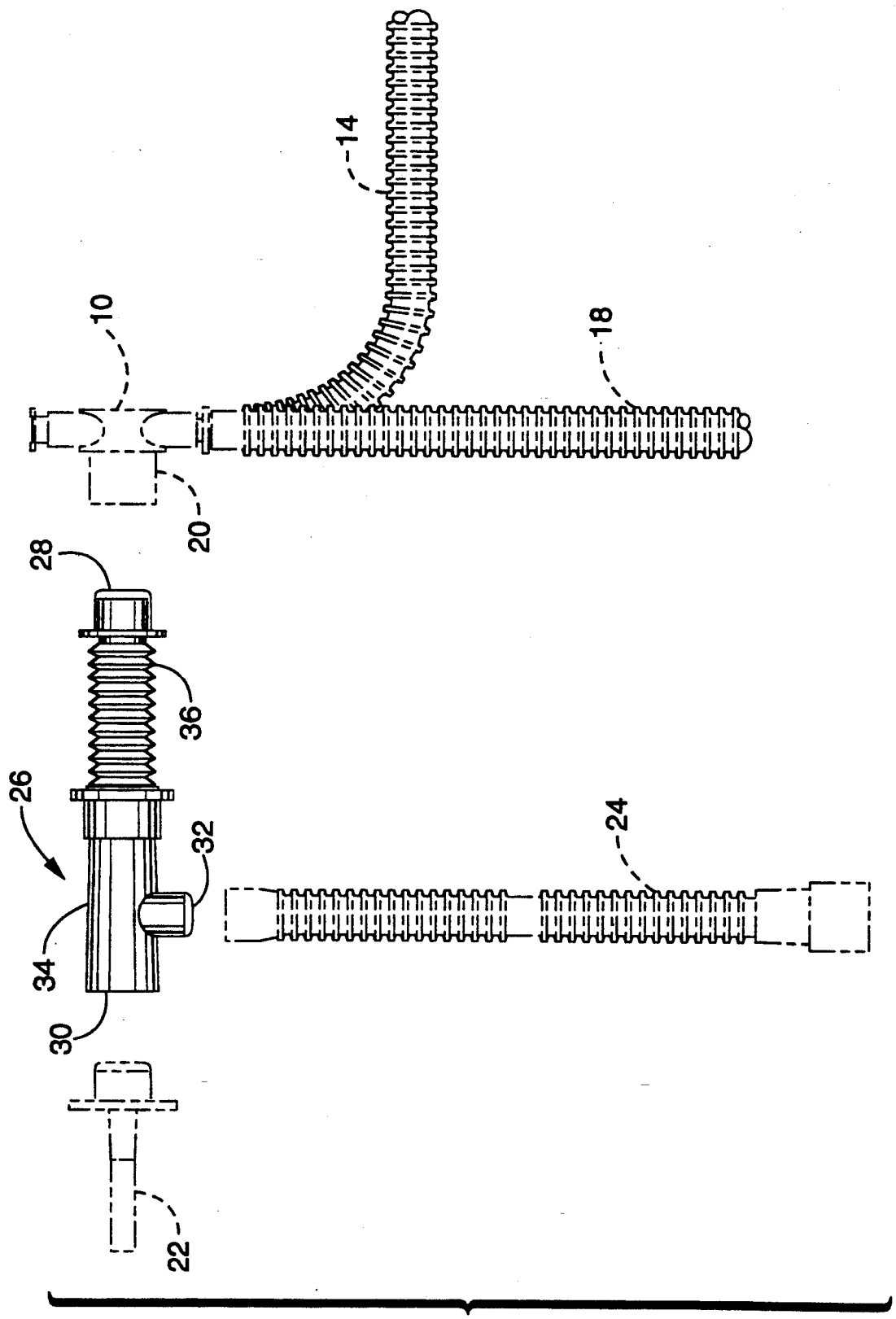
FIG. 3 is an exploded side elevation view of one embodiment of the aerosol delivery system of FIG. 2 showing its placement in relation to a patient wye, aerosol supply tube, and endotracheal tube shown in phantom.
Figure 4:
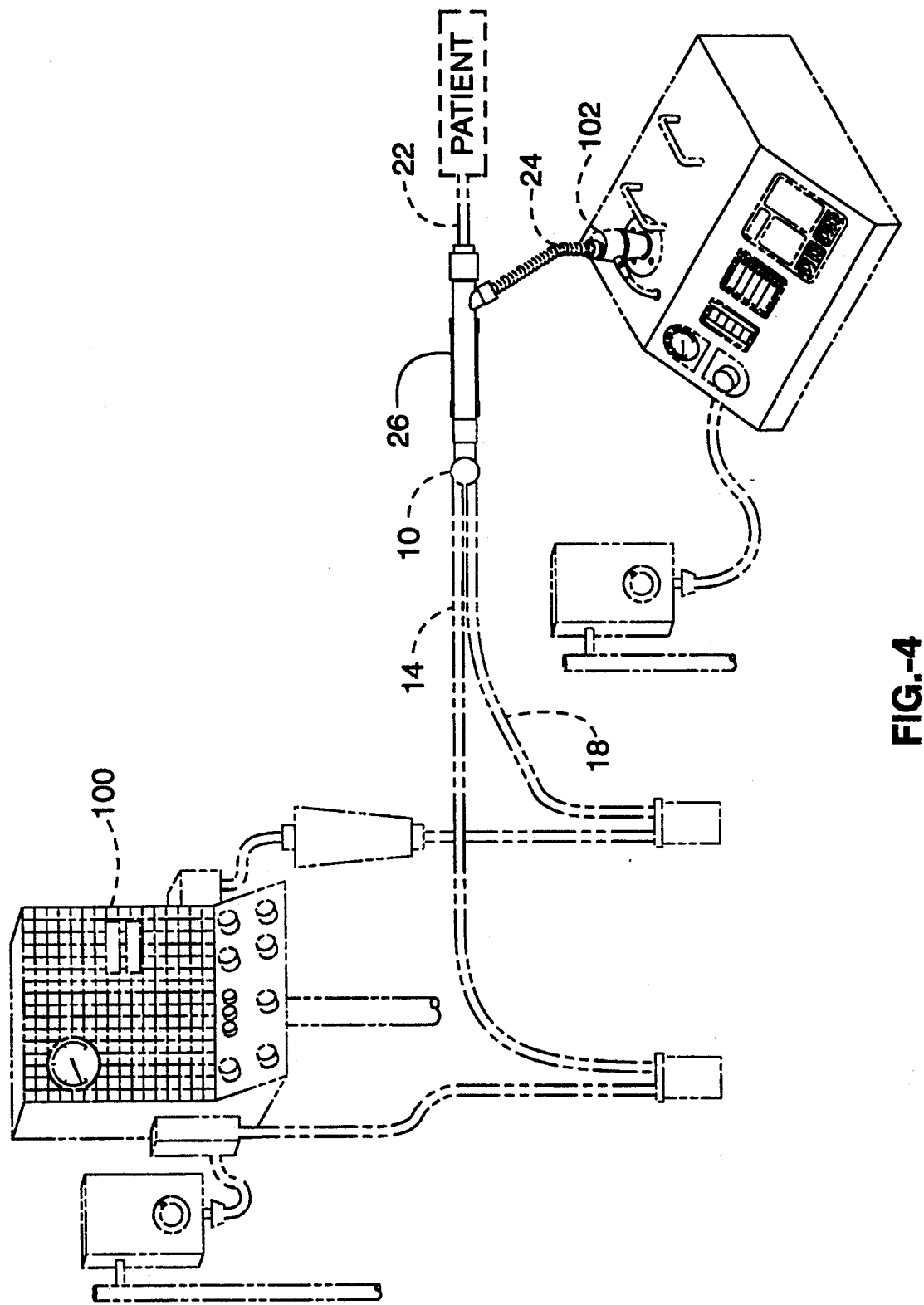
FIG. 4 is a diagrammatic view of the aerosol delivery system of FIG. 3 coupled to a ventilator, nebulizer, and endotracheal tube shown in phantom.

Referring more specifically to the drawings, for illustrative purposes the present invention is embodied in the apparatus which is generally shown in FIG. 2 through FIG. 4 and its method of use. It will be appreciated that the apparatus may vary as to configuration and as to details of the parts without departing from the basic concepts as disclosed herein, and that the method of use may vary as to its steps and their order of implementation without departing from the basic concepts as disclosed herein.

Referring to FIG. 2 and FIG. 4, in accordance with the present invention a charging system 26 is inserted between an endotracheal port 20 of a patient wye 10 and an endotracheal tube 22. Patient wye 10 is typically connected to a ventilator 100 or other respiratory device, and endotracheal tube 22 is fitted into the patient. One end of charging system 26 includes a gas port 28 for coupling the system to ventilator 100. While gas port 28 could be coupled directly to ventilator 100, it is preferably coupled to an endotracheal port 20 in patient wye 10 which is in turn coupled to ventilator 100 through conventional circuitry. The other end of charging system 26 includes a gas port 30 for coupling to an endotracheal tube 22. Charging system 26 also includes an aerosol intake port 32 for coupling to a nebulizer 102 or other device for generating a continuous flow of medicinal aerosol through an aerosol supply hose 24. Aerosol intake port 32 is preferably positioned in proximity to gas port 30.

In the system heretofore described, a continuous flow of medicinal aerosol is delivered through aerosol intake port 32. During the exhalation cycle of ventilation, medicinal aerosol will flow into charging system 26 and toward gas port 28. This filling (or charging) of the system also assists in the flushing of exhaled gas such as $CO_2$ which enters the system during patient exhalation. Preferably the flow of the medicinal aerosol is regulated to eliminate or minimize medicinal aerosol flow into patient wye 10 and out through exhalation tube 18. During the inhalation cycle of ventilation, breathable gas delivered through inhalation tube 14 from the ventilator 100 will flush the medicinal aerosol from charging system 26 and deliver the aerosol to the patient's lungs through endotracheal tube 22. In addition, because a continuous flow of medicinal aerosol is delivered to charging system 26 through aerosol intake port 32, additional amounts of medicinal aerosol will be delivered to the patient from the nebulizer 102 during inhalation. Therefore, aerosol supply hose 24 effectively expands the overall capacity of charging system 26. Once the proper amount of medicinal aerosol is administered, the flow into aerosol intake port 32 can be terminated or charging system 26 can be removed and endotracheal tube 22 connected directly to endotracheal port 20 on patient wye 10.

Referring now to FIG. 3, charging system 26 preferably includes a vessel 34 coupled to a flexible hose 36. Gas port 28 is located at the hose end of the assembly, while gas port 30 is located at the vessel end of the assembly. It is also preferred that aerosol intake port 32 be positioned in proximity to gas port 30 so that medicinal aerosol will fill vessel 34 and hose 36 during patient exhalation rather than be expended into patient wye 10. In addition, the shape of vessel 34 and hose 36 are not critical although, in the preferred embodiment, vessel 34 and hose 36 are of a generally tubular configuration. Furthermore, vessel 34 could be alternatively fashioned from flexible hosing and, while charging system 26 preferably includes hose 36 for adjustability around the patient, it will be appreciated that hose 36 can be eliminated or replaced with a rigid structure.

Therefore, it is noteworthy that the assembly of vessel 34 and hose 36 forms a "charging volume" or "charging vessel" bounded by gas port 28, gas port 30, and aerosol intake port 32, which is filled or "charged" with medicinal aerosol during patient exhalation. While the preferred includes the assembly of vessel 34 and hose 36, effectively any equivalent structure having a chamber which can be filled with medicinal aerosol can be used. And, as previously indicated, aerosol supply hose 24 expands the capacity of charging system 26 since it supplies additional amounts of medicinal aerosol to the patient during inhalation.

Accordingly, it can be seen that this invention provides for delivery of medicinal aerosol to a patient's lungs efficiently and in controlled amounts, while at the same time minimizing or eliminating waste. Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A system for regulating the delivery of medicinal aerosol to a patient being assisted by a respiratory device of the type having a patient wye and an endotracheal tube, comprising: charging volume means for receiving medicinal aerosol from an aerosol generating device during exhalation by a patient, for receiving exhalation gases from said patient, for using said received medicinal aerosol to flush said exhalation gasses from said charging volume means, for storing said received medicinal aerosol, and for delivering said stored medicinal aerosol to said patient during inhalation, said charging volume means including first and second ends, said first end including means for coupling to a respiratory device, said second end including means for coupling to an endotracheal tube, said charging volume means including an aerosol intake port, said aerosol intake port including means for coupling to an aerosol generating device.

2. An apparatus as recited in claim 1, wherein said charging volume includes a generally tubular vessel, said aerosol intake port positioned in said vessel.

3. An apparatus as recited in claim 2, wherein said charging volume includes a flexible hose coupled to said vessel.

4. In an apparatus for delivering medicinal aerosol to a patient, said apparatus including a respiratory device having an inhalation tube, an exhalation tube, and an endotracheal tube, said inhalation tube and said exhalation tube coupled to a patient wye, said patient wye including an endotracheal port for connection to said endotracheal tube, said apparatus including an aerosol generating device for generating medicinal aerosol for delivery to said patient through said endotracheal tube, the improvement comprising: a charging vessel means for receiving medicinal aerosol from an aerosol generating device during exhalation of a patient, for receiving exhalation gases from said patient, for using said received medicinal aerosol to flush said exhalation gasses from said charging vessel means, for storing said received medicinal aerosol, and for delivering said stored medicinal aerosol to said patient during inhalation, said charging vessel means disposed between said endotracheal port and said endotracheal tube, said charging vessel means including an aerosol inlet port for connection to said aerosol generating device.

5. An apparatus as recited in claim 4, wherein said charging vessel includes a flexible hose coupled to said endotracheal port.

6. An apparatus for storing medicinal aerosol during the exhalation stage of a respiratory therapy cycle and delivering said medicinal aerosol to a patient during the inhalation stage of said respiratory therapy cycle, comprising: a generally tubular charging vessel means for receiving medicinal aerosol from an aerosol generating device during exhalation of said patient, for receiving exhalation gases from said patient, for using said received medicinal aerosol to flush said exhalation gasses from said charging vessel means, for storing said received medicinal aerosol, and for delivering said medicinal aerosol to said patient during inhalation, said charging vessel means including a first gas port, said first gas port including means for coupling to a respiratory device, said charging vessel means including a second gas port, said second gas port including means for coupling to an endotracheal tube, said charging vessel means including an aerosol intake port, said aerosol intake port including means for coupling to an aerosol generating device, said aerosol intake port disposed between said first gas port and said second gas port proximal to said second gas port.

7. An apparatus as recited in claim 6, wherein said first gas port includes a flexible coupling.

8. A method for delivering medicinal aerosol to a patient through an endotracheal tube in said patient, comprising the steps of:
   (a) generating a medicinal aerosol;
   (b) providing a continuous flow of said medicinal aerosol to a charging volume means for receiving medicinal aerosol from an aerosol generating device during exhalation of a patient, for receiving exhalation gases from said patient, for using said received medicinal aerosol to flush said exhalation gasses from said charging volume means, for storing said received medicinal aerosol, and for delivering said stored medicinal aerosol to said patient during inhalation, said charging volume means disposed between a respiratory device and an endotracheal tube in a patient assisted by said respiratory device;
   (c) filling said charging volume means with said medicinal aerosol during patient exhalation while flushing exhalation gasses from said charging volume means with said medicinal aerosol; and
   (d) delivering said medicinal aerosol from said charging volume means into said endotracheal tube during patient inhalation.

9. A method as recited in claim 8, further comprising the step of repeating steps (a) through (d).

10. A method as recited in claim 8, further comprising the step of delivering an additional amount of said medicinal aerosol into said endotracheal tube during patient inhalation.

11. A method as recited in claim 8, further comprising the step of delivering a breathable gas into said endotracheal tube during said inhalation by said patient.

12. A process for administering medicinal aerosol to a patient's lungs through an endotracheal tube connected to a respiratory device, comprising the steps of:
   (a) inserting a charging vessel means for receiving medicinal aerosol from an aerosol generating device during exhalation of a patient, for receiving exhalation gases from said patient, for using said received medicinal aerosol to flush said exhalation gasses form said charging vessel means, for storing said received medicinal aerosol, and for delivering said stored medicinal aerosol to said patient during inhalation between an endotracheal tube and a respiratory device;
   (b) connecting said charging vessel means to an aerosol generating device;
   (c) injecting medicinal aerosol into said charging vessel means during patient exhalation while flushing exhalation gasses from said charging volume means with said medicinal aerosol; and
   (d) discharging said medicinal aerosol from said charging vessel means into said endotracheal tube during patient inhalation.

13. A process as recited in claim 12, further comprising the step of delivering an additional amount of said medicinal aerosol into said endotracheal tube during said patient inhalation.

14. A method as recited in claim 13, further comprising the step of delivering a breathable gas into said endotracheal tube during said patient inhalation.

* * * * *